United States Patent
Utsugida et al.

(10) Patent No.: US 9,889,245 B2
(45) Date of Patent: Feb. 13, 2018

(54) CIRCULATION APPARATUS AND METHOD FOR CONTROLLING SAME

(71) Applicant: TERUMO KABUSHIKI KAISHA, Shibuya-ku, Tokyo (JP)

(72) Inventors: Tomoki Utsugida, Kanagawa (JP); Ryosuke Hanai, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 157 days.

(21) Appl. No.: 14/868,484

(22) Filed: Sep. 29, 2015

(65) Prior Publication Data

US 2016/0015883 A1 Jan. 21, 2016

Related U.S. Application Data (63) Continuation of application No. PCT/JP2013/002213, filed on Apr. 1, 2013.

(51) Int. Cl.
*A61M 1/36* (2006.01)
*A61M 1/16* (2006.01)

(52) U.S. Cl.
CPC ........ *A61M 1/3666* (2013.01); *A61M 1/1601* (2014.02); *A61M 1/1698* (2013.01);
(Continued)

(58) Field of Classification Search
CPC .............. A61M 1/1601; A61M 1/1698; A61M 2205/3334; A61M 2205/3368;
(Continued)

(56) References Cited

U.S. PATENT DOCUMENTS 8,632,485 B2 * 1/2014 Schlaeper ............ A61B 5/0002
210/645
2006/0074369 A1 4/2006 Oishi et al.
(Continued)

FOREIGN PATENT DOCUMENTS

JP 53-101893 A 9/1978
JP 2006-325750 A 12/2006
(Continued)

OTHER PUBLICATIONS

Extended European Search Report dated Oct. 27, 2016, issued by the European Patent Office in corresponding European Application No. 13881291.2. (11 pages).
International Search Report (PCT/ISA/210) dated May 7, 2013, by the Japanese Patent Office as the International Searching Authority for International Application No. PCT/JP2013/002213.

*Primary Examiner* — Leslie Deak
(74) *Attorney, Agent, or Firm* — Buchanan Ingersoll & Rooney PC (57) ABSTRACT

A highly reliable circulation apparatus promptly detects an abnormal state of a status value related to blood flowing in a circulation circuit with no particular operation performed. As an extracorporeal circulation mode starts, a user operates a pump first and waits until a flow rate is stabilized. Then, when the flow rate is stabilized, a predetermined value is added to or subtracted from the stabilized flow rate so as to set two threshold values which regulate an upper end and a lower end of a permissible state range. Then, it is monitored whether or not the flow rate is within the permissible state range regulated by the threshold values, and when the flow rate deviates from the permissible state range, an alarm is issued for notification.

15 Claims, 4 Drawing Sheets

(52) U.S. Cl.
CPC ........ *A61M 1/3626* (2013.01); *A61M 1/3667*
(2014.02); *A61M 2205/18* (2013.01); *A61M
2205/3331* (2013.01); *A61M 2205/3334*
(2013.01); *A61M 2205/3355* (2013.01); *A61M
2205/3368* (2013.01); *A61M 2205/3606*
(2013.01)

(58) Field of Classification Search
CPC .......... A61M 2230/30; A61M 2230/50; A61B
5/0002; G06F 19/3418
See application file for complete search history.

(56) References Cited

U.S. PATENT DOCUMENTS

| | | |
|---|---|---|
| 2007/0126706 A1 | 6/2007 | Ziegler et al. |
| 2011/0269167 A1 | 11/2011 | Bene |
| 2012/0010554 A1* | 1/2012 | Vantard ................. A61M 1/16 604/6.04 |
| 2012/0273415 A1 | 11/2012 | Gerber et al. |

FOREIGN PATENT DOCUMENTS

| | | |
|---|---|---|
| JP | 2007-512060 A | 5/2007 |
| JP | 2007-167109 A | 7/2007 |
| JP | 2010-063644 A | 3/2010 |
| WO | 2007/072773 A1 | 6/2007 |

\* cited by examiner

CIRCULATION APPARATUS AND METHOD FOR CONTROLLING SAME

CROSS-REFERENCES TO RELATED APPLICATIONS

This application is a continuation of International Application No. PCT/JP2013/002213 filed on Apr. 1, 2013, the entire content of which is incorporated herein by reference.

TECHNICAL FIELD

The present invention relates to a circulation apparatus and a method of controlling the same.

BACKGROUND DISCUSSION

Generally, in an extracorporeal circulation apparatus such as the artificial heart-lung machine described in JP-A-2006-325750, a status value related to blood flowing inside a circulation circuit is obtained and monitored. Furthermore, a device in the apparatus, such as the pump provided in the circulation circuit of the machine described in JP-A-2006-325750, is controlled based on the result thereof.

In utilizing such an extracorporeal circulation apparatus, the pump can be operated by setting a flow rate (volume of flowing blood per unit time) in which a physique and the like of a patient are considered. In addition, a flow rate sensor provided on the circulation circuit detects the actual flow rate, and threshold values (an upper limit value and a lower limit value) for determining whether the flow rate is appropriate are also set. Furthermore, the apparatus can have a feature in which, when the flow rate detected by the sensor falls below the set lower limit value, an appropriate automated function such as issuance of an alarm is triggered.

SUMMARY

However, the operator may forget to set the threshold values, particularly since a pump in operation can generally be visually confirmed. In addition, even if the threshold values are set, normal operation has been presumed as long as a flow rate detected by a sensor is within a set range between an upper limit value and a lower limit value. Therefore, sudden fluctuation of the flow rate or a tendency of deviating from the range between the upper limit value and the lower limit value has not been detected in advance.

In taking the above-described circumstances into consideration, there is provided a highly reliable circulation apparatus which promptly detects an abnormal state of a status value related to blood flowing in a circulation circuit with no particular operation performed.

In order to achieve the above-described and other objectives, a circulation apparatus includes a constitution as described below. That is, a circulation apparatus which causes blood of a patient to circulate outside a human body by using a circulation circuit, the apparatus including detecting means for detecting a status value related to blood while being provided on a flow path through which blood flows in the circulation circuit, determining means for determining whether or not a stable state in which the status value exhibits transition within a range set in advance is achieved after the circulation circuit starts blood circulation, setting means for setting two threshold values which respectively regulate an upper end and a lower end of a permissible state range based on the status value in the stable state when the determining means determines that the stable state is achieved, monitoring means for monitoring whether or not the status value is within the permissible state range which is regulated by the two threshold values, after the stable state is achieved, and warning means for issuing an alarm when the monitoring means detects that the status value deviates from the permissible state range.

Accordingly, there is provided a highly reliable circulation apparatus which promptly detects an abnormal state of a status value related to blood flowing in a circulation circuit with no particular operation performed.

Other characteristics and advantages will be clearly described with reference to the accompanying drawings. In the accompanying drawings, the same or similar constitutions will be applied with the same reference numerals and signs.

BRIEF DESCRIPTION OF THE DRAWINGS

The accompanying drawings illustrate exemplary embodiments of the present disclosure.

DETAILED DESCRIPTION

Hereinafter, embodiments of the present disclosure will be described in detail with reference to the accompanying drawings.

First Embodiment

<1. Overall Constitution of Extracorporeal Circulation Apparatus>

Figure 1:
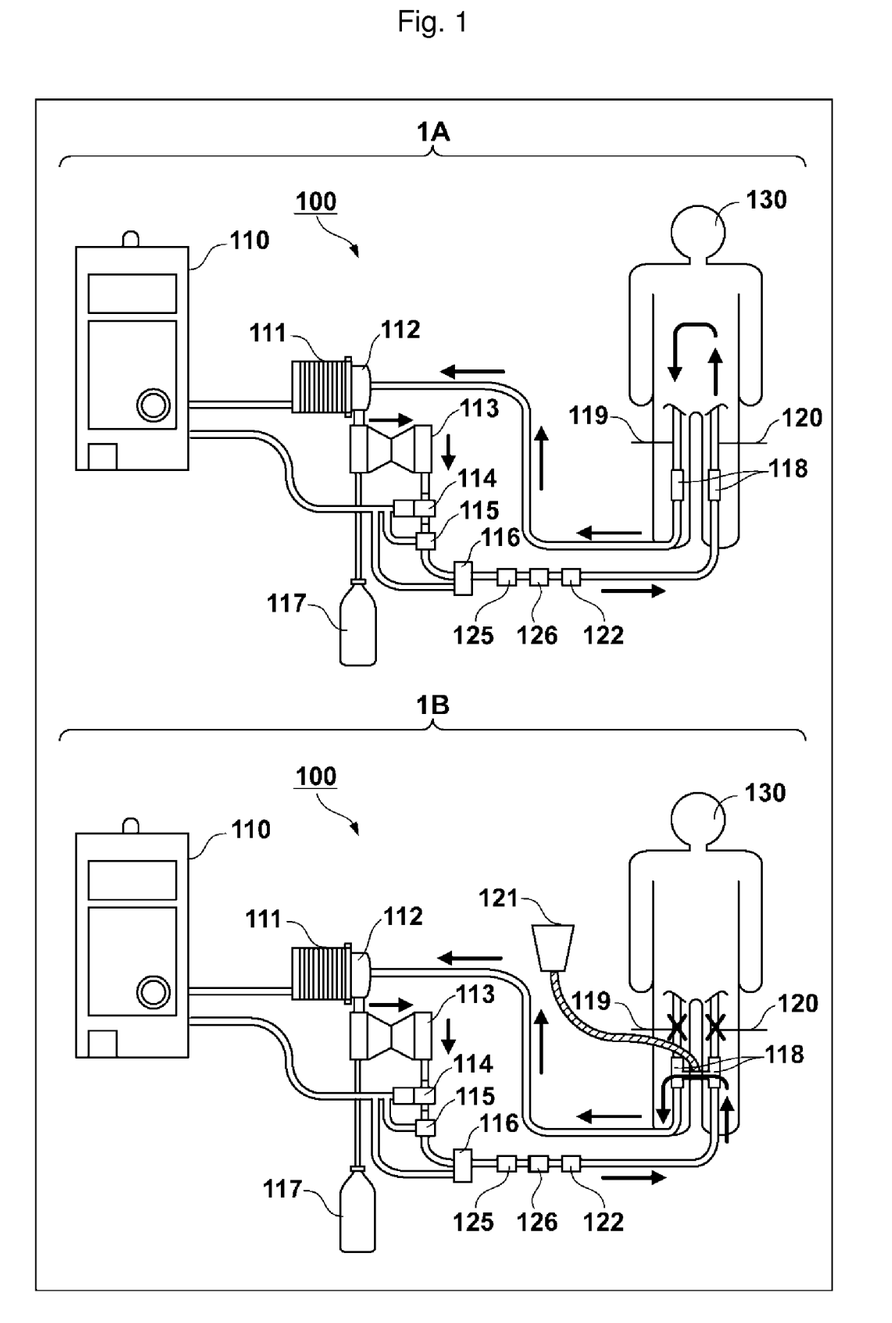
FIG. 1 is a diagram illustrating an overall constitution of an extracorporeal circulation apparatus in an embodiment.

First, an overall constitution of an extracorporeal circulation apparatus according to an embodiment will be described. FIG. 1 illustrates an example of an overall constitution of an extracorporeal circulation apparatus 100 in a circulation state 1a and a priming state 1b in the embodiment.

The extracorporeal circulation apparatus 100 is used in auxiliary circulation techniques such as percutaneous cardiopulmonary support (PCPS), extracorporeal membrane oxygenation (ECMO), and the like. The extracorporeal circulation apparatus 100 includes a blood extracorporeal circulation circuit (hereinafter, referred to as the circulation circuit) indicated by arrows in the diagram. In the extracorporeal circulation apparatus 100, after a priming operation is performed, blood of a patient 130 is subjected to extracorporeal circulation by using the circulation circuit.

The priming operation denotes an operation in which a priming liquid circulates inside the circulation circuit so as to eliminate air bubbles inside the circuit in a state where the circulation circuit is sufficiently filled with the priming liquid (for example, a physiological salt solution).

The extracorporeal circulation apparatus 100 includes a controller 110 which functions as a control device, a drive motor 111, a centrifugal pump 112, an artificial lung 113, an oxygen supply source 117, a cannula (vein side) 119, a cannula (artery side) 120, an air bubble sensor 114, a flow rate sensor 115, a blood filter 116, branch lines 118, a clamp 122, a pressure sensor 125, and a temperature sensor 126. Each of the constitutions is connected to one another through flexible tubes and the like, and each lumen of the tubes constitutes a flow path of blood or the priming liquid.

The cannula (artery side) 120 performs blood transmission into the body of the patient 130, and the cannula (vein side) 119 performs blood extraction from the inside of the body of the patient 130.

The centrifugal pump 112 (also referred to as the centrifugal artificial heart) drives a rotary body provided therein so as to apply pressure to blood, thereby causing the blood to circulate inside the circulation circuit. The drive motor 111 applies a rotary drive force to the rotary body of the centrifugal pump 112.

The artificial lung 113 performs circulation of blood and gas exchange (oxygenation, carbon dioxide elimination, and the like) of blood. For example, the oxygen supply source 117 is realized with an oxygen cylinder or the like and supplies oxygen which is added to blood. The oxygen supplied from the oxygen supply source 117 is used during gas exchange which is performed by the artificial lung 113.

The air bubble sensor 114 detects air bubbles which are included in the priming liquid or blood flowing inside the circulation circuit at the time of the priming operation and the extracorporeal circulation operation by a predetermined detection method (ultrasound, light, or the like). The blood filter 116 filters blood and eliminates air bubbles in blood. The flow rate sensor 115 is constituted to have a built-in ultrasound transceiver, for example, and detects a flow rate of the priming liquid or blood inside the circulation circuit. The pressure sensor 125 detects pressure of blood sent from the pump, and the temperature sensor 126 measures a temperature of blood.

The clamp 122 is a member which blocks the tubes so as to forcedly stop blood transmission into the body of the patient 130 at the time of the extracorporeal circulation operation. The clamp 122 can automatically perform a blocking operation in an interlocking manner when an occurrence of abnormality requiring an immediate stop of blood transmission is determined based on an output signal from the air bubble sensor 114.

The branch lines 118 switch the flow path of the circulation circuit. Specifically, at the time of the extracorporeal circulation operation in which blood of the patient 130 is subjected to extracorporeal circulation, as illustrated in circulation state 1A of FIG. 1, the circulation circuit passing through the inside of the body of the patient 130 is established, thereby causing blood to circulate outside the body of the patient 130. At the time of the priming operation, as illustrated in priming state 1B of FIG. 1, the path of the circulation circuit into the body of the patient 130 is shut off by the branch lines 118 so as to establish the circulation circuit passing through only the outside of the body of the patient 130 (in other words, the circulation circuit not passing through the inside of the patient 130) and the inside of the circulation circuit is filled with the priming liquid, thereby causing the priming liquid to circulate therein (without passing through the inside of the patient). One or a plurality of air bubble discharge ports (not illustrated) for discharging air bubbles are provided on the circulation circuit. As the priming liquid circulates inside the circulation circuit for a plurality of laps, air bubbles inside the circulation circuit are discharged through the air bubble discharge port.

The controller 110 performs integrated controlling of the extracorporeal circulation operation and the priming operation of the extracorporeal circulation apparatus 100. For example, the controller 110 controls the drive motor 111 so as to drive the centrifugal pump 112. In addition, the controller 110 controls the air bubble sensor 114 to obtain an output signal from the air bubble sensor 114 or controls the flow rate sensor 115 to obtain a flow rate value. Moreover, in an extracorporeal circulation operation mode, when abnormality requiring a stop of blood transmission is detected based on the output signal from the air bubble sensor 114, the clamp 122 is in a blocking operation.

Subsequently, with reference to the extracorporeal circulation apparatus 100 illustrated in FIG. 1, descriptions will be given in a simple manner regarding a flow of processing when performing a cardiopulmonary support operation (an extracorporeal circulation operation and a priming operation).

As the cardiopulmonary support operation starts, the controller 110 controls execution of the priming operation. At the time of the priming operation, as illustrated in priming state 1B of FIG. 1, the circulation circuit not passing through the inside of the body of the patient 130 is established by the branch lines 118. In addition, in this case, a priming liquid supply source 121 is connected to the branch lines 118, and the priming liquid is supplied to the inside of the circulation circuit from the priming liquid supply source 121. In this manner, the inside of the circulation circuit is filled with the priming liquid.

Then, the centrifugal pump 112 is controlled to be driven by the controller 110, and the priming liquid circulates inside the circulation circuit for the plurality of laps. Air bubbles inside the circulation circuit are discharged through the air bubble discharge port and the like. In addition, the presence or absence of air bubbles flowing inside the circulation circuit may be detected by the air bubble sensor 114 at the time of the priming operation.

A user who has confirmed completion of priming stops driving of the centrifugal pump and switches the branch lines 118, thereby establishing the circulation circuit passing through the inside of the body of the patient 130 as illustrated in circulation state 1A of FIG. 1. Thereafter, the user operates the controller 110 so as to set a target flow rate and inputs an instruction to start extracorporeal circulation. As a result, as the controller 110 drives the pump 112 based on the set information, blood of the patient 130 is in extracorporeal circulation.

As the extracorporeal circulation operation starts, blood subjected to blood extraction through the cannula (vein side) 119 flows into the artificial lung 113 via the centrifugal pump 112. In the artificial lung 113, as described above, processing of gas exchange, that is, oxygenation, carbon dioxide elimination, and the like are performed. Thereafter, blood which is filtered via the blood filter 116 and the like is subjected to blood transmission into the body of the patient 130 through the cannula (artery side) 120. The flowing of blood of the patient 130 from the cannula (vein side) 119 to the cannula (artery side) 120 is continuously performed. In the extracorporeal circulation operation mode, processing is performed in accordance with signals from the various sensors. For example, when air bubbles inside the circulation circuit are detected by the air bubble sensor 114 and there is a need to stop blood transmission, the blocking operation of the clamp 122 is performed.

Hereinbefore, descriptions are given regarding the example of the overall constitution of the extracorporeal circulation apparatus 100 and flowing of the cardiopulmonary support operation in the present embodiment. However, the constitutions of the extracorporeal circulation apparatus 100 illustrated in FIG. 1 are merely examples, and thus, the constitutions may be appropriately changed.

<2. Functional Constitution of Controller>

Figure 2:
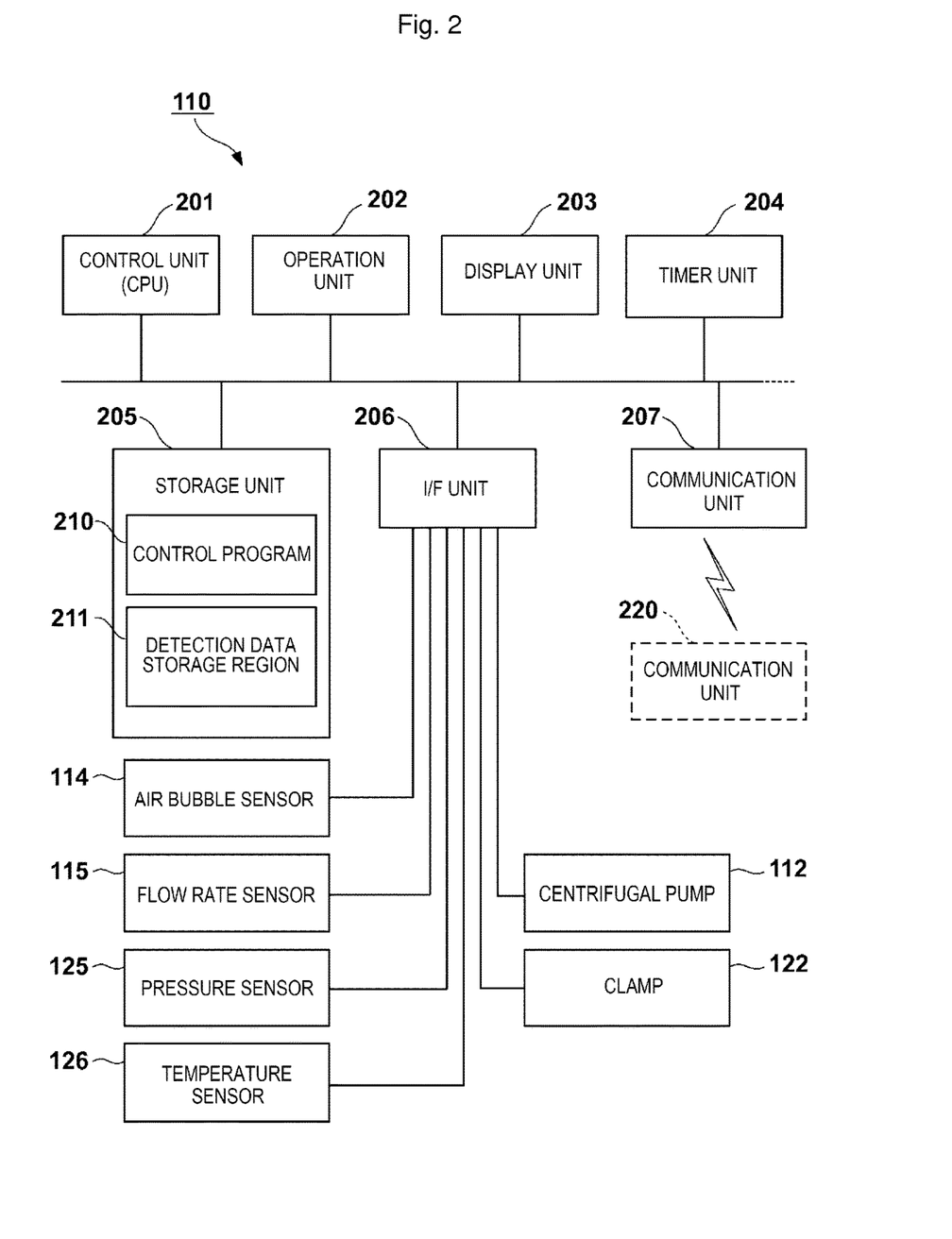
FIG. 2 is a diagram illustrating an example of a functional constitution of a controller of the extracorporeal circulation apparatus.

Subsequently, with reference to FIG. 2, descriptions will be given regarding an example of the functional constitution of the controller 110 illustrated in FIG. 1.

As the functional constitution thereof, the controller 110 includes a control unit 201, an operation unit 202, a display unit 203, a timer unit 204, a storage unit (a recording medium which can be read by a computer) 205, an I/F unit 206, and a communication unit 207.

The control unit 201 constituted of a central processing unit (CPU) controls the controller 110 and also controls the circulation circuit.

For example, the operation unit 202 is realized with various buttons and the like, and a health care worker inputs instruction therethrough. For example, the display unit 203 is realized with a display device such as a monitor and the like (including an output unit which outputs an audio warning) and displays various items of information (including a message) to a user. A portion or the entirety of the operation unit 202 and the display unit 203 may be realized in a touch panel with an audio speaker, for example.

The timer unit 204 performs timekeeping for various time periods. For example, the storage unit 205 is realized with ROM, RAM, and the like and includes a control program 210 for realizing the extracorporeal circulation operation mode in order to perform an operation as the circulation apparatus, and a detection data storage region 211 for storing detection results detected by each sensor. As the control program related to a continuous operation mode is executed, the control unit 201 executes the above-described priming processing and subsequently inputs setting of a target flow rate from the operation unit 202, thereby executing driving control of the pump 112 via the I/F unit 206 or processing of extracorporeal circulation in accordance with the detection results of the various sensors.

The communication unit 207 performs communication with a communication unit 220 with which a health care worker is equipped. Communication between the communication unit 207 and the communication unit 220 may be short-range radio communication such as Bluetooth (registered trademark) and the like, or radio communication through wireless LAN such as Wi-Fi and the like.

Hereinbefore, descriptions are given regarding the example of the functional constitution of the controller 110. The functional constitution illustrated in FIG. 2 is merely an example. Thus, a new constitution may be added, and an unnecessary constitution may be appropriately omitted.

The present embodiment is characterized in processing of an alarm based on the flow rate during execution of the extracorporeal circulation operation mode after the priming processing. Therefore, hereinafter, descriptions will be given regarding the extracorporeal circulation operation mode.

<3. Overview of Extracorporeal Circulation Operation Mode on Basis of Output Signal from Flow Rate Sensor>

In the present embodiment, similar to that in the related art, a user sets the target flow rate, as well as an upper limit value TH_max and a lower limit value TH_min of the flow rate. Then, when the flow rate sensor 115 detects a flow rate which exceeds the upper limit value TH_max or a flow rate which falls below the lower limit value TH_min, an emergency alarm is issued for notification. For example, the notification is performed by generating a warning sound from a speaker (not illustrated) or displaying a message on a screen indicating the emergency alarm.

However, there is a possibility that the upper limit value TH_max and the lower limit value TH_min are forgotten to be set. In addition, according to current technology in which only setting of the upper limit value TH_max and the lower limit value TH_min is performed, a warning of the emergency alarm is issued only when the flow rate is out of the range which is regulated by the values. Therefore, in such a case where the flow rate slowly drops, there is no notification of the emergency alarm as long as the flow rate is equal to or greater than the lower limit value TH_min. In other words, a long period of time elapses until the flow rate falls below the lower limit value TH_min, and only then, a warning is issued. Such circumstances are often caused when the artificial lung 113 is gradually clogged and vascular resistance inside the circulation circuit increases. In such circumstances, measures are taken by replacing the artificial lung 113, for example. However, if a symptom thereof can be recognized in advance, it is possible to start preparing a flushing operation before falling below the lower limit value TH_min.

In addition, although the flow rate is within the range between the upper limit value TH_max and the lower limit value TH_min, there is a problem in that it is not possible to perceive significant variation of the flow rate occurring in a short period of time. A representative factor of the problem is that the tubes constituting the circulation circuit are bent by an external force. When a bent state of the tubes continues, the flow rate falls below the lower limit value TH_min, and it is clear and desirable to take prompt countermeasures.

In the present embodiment, even though the flow rate is within the range between the upper limit value TH_max and the lower limit value TH_min, or the upper limit value TH_max and the lower limit value TH_min are forgotten to be set, variation of the flow rate which gradually varies in a temporal manner and variation of the flow rate which significantly varies in a temporal manner are detected, and an alarm warning is performed with respect to them as well. Moreover, the processing is realized with no particular operation performed by a use. The alarm described herein is not urgent as much as the above-described emergency alarm. Therefore, hereinafter, it will be referred to as the moderate alarm. The notification of the moderate alarm is acceptable as long as the moderate alarm can be distinguished from the emergency alarm. The speaker is driven in a lower key compared to that of the emergency alarm, or notification is issued by controlling a display.

In the embodiment, in order to realize detection and notification of the moderate alarm, the control unit 201 of the circulation apparatus performs two types of processing described below.

1. Execution of the extracorporeal circulation operation mode starts. When it is detected that the flow rate is stabilized within the range set in advance, a threshold value TH_H which is obtained by adding a value set in advance to the flow rate at that time and a threshold value TH_L which is obtained by subtracting a value set in advance from the same are decided. Here, the values are under a relationship of TH_min<TH_L<TH_H<TH_max. Then, after the threshold value TH_H and the threshold value TH_L are decided, when the flow rate detected by the flow rate sensor 115 deviates from the range, a warning of the moderate alarm for alerting is issued. Accordingly, it is possible to notify a user of a blood flow which gradually varies due to the factors such as gradual clogging and the like of the artificial lung 113 and to alert the user before the flow rate falls below the lower limit value.

2. After the threshold values TH_H and TH_L are decided, variation of the flow rate (a difference between the flow rate of the previous detection and the flow rate of the current detection, that is, a differential of the flow rate with respect to a time axis) which is detected by the flow rate sensor 115 is monitored. Then, when there is variation exceeding a predetermined threshold value, a warning of the moderate alarm is issued. As a result, bending or the like of the tubes can be detected, and thus, immediate countermeasures can be performed.

Figure 3:
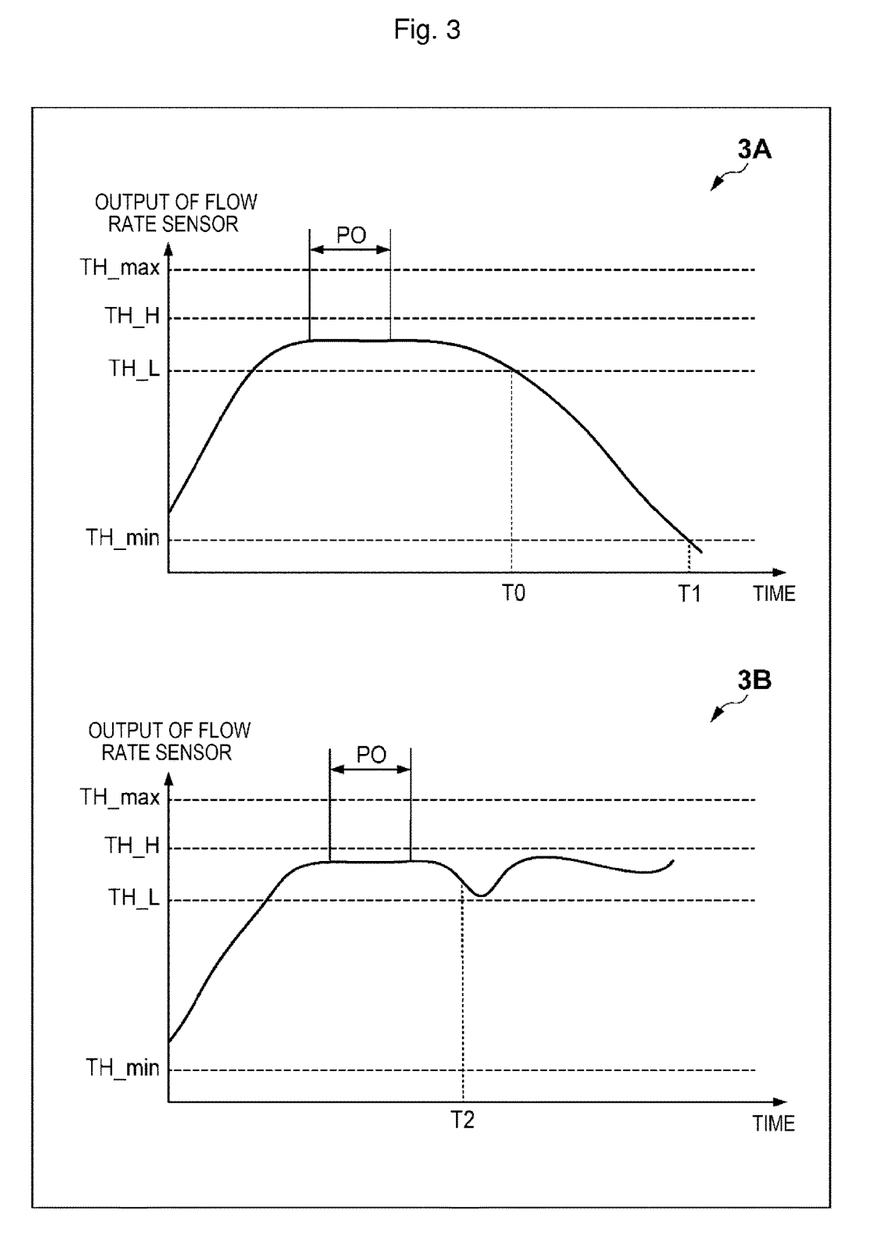
FIG. 3 is a diagram for illustrating an example of transition of a flow rate sensor during an extracorporeal circulation operation mode.

In order to make the above-described processing easier to be understood, descriptions will be given with reference to examples 3A and 3B of FIG. 3. In FIG. 3, the horizontal axis indicates the time axis, and the vertical axis indicates the flow rate. A sampling period of the flow rate detected by the flow rate sensor 115 is set to 50 msec, and an average value of the latest N flow rate values (in the embodiment, N=10) is detected as a current flow rate value V. It is because there is slight fluctuation in the values detected by the flow rate sensor 115. The latest N items of data are held in the detection data storage region 211.

In example 3A of FIG. 3, as the extracorporeal circulation operation mode starts, the centrifugal pump 112 is in operation by driving the drive motor 111. As a result, a flow of blood is generated in the circulation circuit, and the flow rate V detected by the flow rate sensor 115 gradually increases. Then, when a difference between the maximum value and the minimum value of the flow rate value V which are detected during a predetermined time period P0 (in the embodiment, P=two seconds) is equal to or less than a value ε set in advance, the flow rate becomes substantially uniform, thereby being presumed to be in a stable state. In the embodiment, the value ε is set to "1 L/min". When the stable state is detected, a value set in advance (in the embodiment, 2 L/min) is added to and is subtracted from the flow rate value representing the average value (or a median value) thereof, thereby deciding two threshold values TH_H and TH_L. Since then, every time the flow rate value V is acquired by the flow rate sensor 115, the control unit 201 determines whether or not Condition: $TH\_L \leq V \leq TH\_H$ is fulfilled. When the condition is fulfilled, it is determined to be in the stable state. When the aforementioned condition is not fulfilled, that is, when the current flow rate V exceeds the threshold value TH_H or falls below the threshold value TH_L, the moderate alarm is issued.

As a result thereabove, for example, when the artificial lung 113 is gradually clogged and the flow rate gradually drops, it is possible to issue notification of the moderate alarm at a timing T0. As a result, a user can be alerted at a timing much earlier than a timing T1 for reaching the lower limit value.

Moreover, in the embodiment, it is possible to detect variation of the flow rate which is relatively significant. Therefore, in determining whether or not the flow rate is relatively significant, the determination is performed as follows.

When a current flow rate is represented by $V_i$, a preceding flow rate which is acquired one before $V_i$ (before 50 msec) is represented by $V_{i-1}$, a difference (a differential) "$V_i - V_{i-1}$" thereof is defined as Di, and a positive value indicating permissible variation of the flow rate set in advance is represented by ΔTH, and when the condition of $Di-4, Di-3, Di-2, Di-1,$ and $Di < -\Delta TH$ (1)

or $Di-4, Di-3, Di-2, Di-1,$ and $Di > \Delta TH$ (2)

is fulfilled, it is determined to be in an abnormal state, thereby issuing the moderate alarm. Here, the aforementioned condition (1) indicates that "the flow rate drops at a speed exceeding the permissible variation of the flow rate five times in a row", that is, the flow rate is significantly dropping. In addition, the condition (2) indicates that "the flow rate rises at a speed exceeding the permissible variation of the flow rate five times in a row", that is, the flow rate is significantly rising. The number "5" in a row adopted herein is an example, and the number may be suitably revised.

Example 3B of FIG. 3 illustrates that a drop of the flow rate occurred in a short period of time is detected at a timing T2, for example, by performing the above-described processing after the time period P0 which is determined as the stable state. Since the moderate alarm is issued at the timing T2, a user can be alerted so as to recheck the position where the tubes are placed, for example. The diagram also illustrates an example in which, a user performs an operation of aligning the positions of the tubes, for example, thereby restoring the stable state again.

As is clear in the above description, even if there is an occurrence of a circumstance in which the tubes are slowly bent at a speed which corresponds to none of the aforementioned conditions (1) and (2), the circumstance is in a state equivalent to the state of example 3A of FIG. 3. As a result, it is possible to issue the moderate alarm at a stage in which the flow rate falls below the threshold value TH_L.

<4. Flow of Processing of Extracorporeal Circulation Operation Mode>

Figure 4:
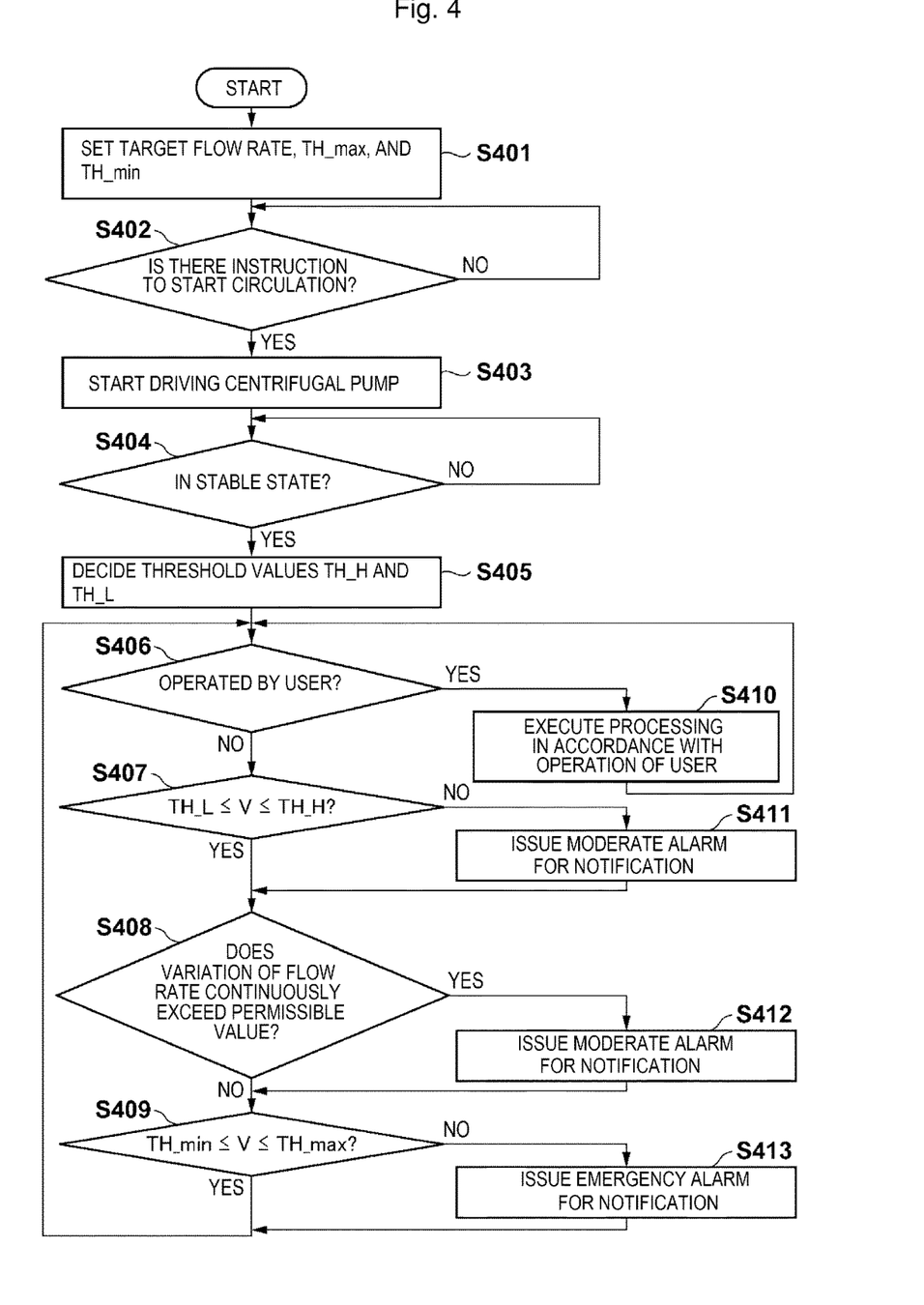
FIG. 4 is a flow chart illustrating a flow of control processing of the controller in the embodiment.

Taking the above descriptions into consideration, descriptions will be given in accordance with a flow chart in FIG. 4 regarding the contents of processing in the extracorporeal circulation operation mode of the control unit 201 in the extracorporeal circulation apparatus 100 of the embodiment. FIG. 4 shows a portion inside the control program 210 of FIG. 2. Hereinafter, in order to make the description simple, descriptions will be focused on the processing based on the flow rate detected by the flow rate sensor 115.

When the priming processing ends and the extracorporeal circulation operation mode starts, in Step S401, a user first performs an operation with respect to the operation unit 202, thereby setting the target flow rate, the upper limit value TH_max, and the lower limit value TH_min. Then, the user waits an instruction to start extracorporeal circulation (Step S402).

When the instruction to start thereof is detected, the processing proceeds to Step S403. Then, the drive motor 111 is driven based on the set flow rate, thereby starting the operation of the centrifugal pump 112. Thereafter, it is determined whether or not the flow rate V detected by the flow rate sensor 115 is in the vicinity of the set target flow rate while being in the stable state, based on a signal from the flow rate sensor 115. This determination is made based on that the difference with respect to the target flow rate is equal to or less than the permissible value, and whether or not the difference between the maximum value and the minimum value of the flow rate within the latest predetermined time period (in the embodiment, two seconds) is equal to or less than the value ε set in advance, as described above.

When it is judged to be in the stable state, the processing proceeds to Step S405, thereby deciding the threshold values TH_H and TH_L for determining whether or not the moderate alarm is issued.

Then, in the midst of extracorporeal circulation, the determination processing (monitoring processing) of Steps S406 to S409 is performed. When normal extracorporeal circulation is performed, the determination processing of Steps S406 to S409 is repeated. Then, when a surgical operation is over, as an instruction thereof is performed, the processing proceeds to Step S410, thereby performing the ending processing. Step S410 includes various types of processing. For example, instruction of stopping the moderate alarm, and the like is one of the processing thereof.

While the extracorporeal circulation processing is in progress, when it is judged that a relationship between the detected flow rate V, and the threshold values TH_L and TH_H is V<TH_L or V>TH_H, the processing proceeds from Step S407 to Step S411, thereby performing the processing to issue the moderate alarm. The notification of an alarm continues until a user cancels the notification in Step S410.

In addition, while the extracorporeal circulation processing is in progress, when it is determined that all of five latest differential values {Di−4, Di−3, Di−2, Di−1, and Di} including the current flow rate differential value Di are smaller than the permissible variation −ΔTH of the flow rate set in advance or are greater than ΔTH, it is judged that the flow rate has varied suddenly and significantly, thereby performing the processing to issue the moderate alarm in Step S412. Even though both Steps S411 and S412 are the processing to issue the moderate alarm, the state thereof is different from each other. Therefore, it is desirable to issue the moderate alarms so as to be able to distinguish the alarms from each other. For example, in Steps S411 and S412, the factors thereof are different from each other. Therefore, a message for checking predicted points with respect thereto may be prepared and displayed.

In addition, while the extracorporeal circulation processing is in progress, when the current flow rate V exceeds the upper limit value TH_max or falls below the lower limit value TH_min, the processing to issue the emergency alarm is performed in Step S413.

As described above, according to the extracorporeal circulation apparatus 100 of the present embodiment, the upper limit value and the lower limit value of the flow rate allow to detect a symptom before the emergency alarm is generated. When the symptom is detected, a user can be notified of the detected symptom. Moreover, a user can be notified with no particular operation more than the operation which has been performed so far.

Second Embodiment

In the first embodiment, descriptions are given regarding the example of the flow rate by using the flow rate sensor 115. However, similar processing can be performed with a pressure value detected by the pressure sensor 125. In other words, even though the centrifugal pump 112 is in operation, when clogging is generated at any place inside the circulation circuit, the pressure value in the pump gradually increases on the downstream side. In addition, it is because the pressure increases even when the tubes are bent or are stepped. When performing the processing with the pressure sensor 125, the pressure sensor 125 may replace the flow rate sensor 115 which is adopted in the above-described embodiment. However, it is necessary to pay attention to the point that the various threshold values are set to the values corresponding to the pressure values.

Third Embodiment

There is hypothermia treatment as a method of treating a patient. A surgical operation is performed by lowering a body temperature. In this case, while lowering the body temperature of a patient, the surgical operation is performed by installing a cooling device for cooling blood to be replaced inside the patient between a downstream place of the centrifugal pump 112 in the circulation circuit and an upstream place of the temperature sensor 126. Here, the embodiment may be applied to a case where the temperature sensor 126 detects whether or not cooling is appropriately performed by the cooling device. When performing with the temperature sensor 126, the temperature sensor 126 may replace the flow rate sensor 115 which is adopted in the above-described embodiment. However, it is necessary to pay attention to the point that the various threshold values are set to the values corresponding to the temperatures.

Other Embodiments

In the above-described embodiment, the function is performed by a program executed by the control unit 201 inside the controller 110 which functions as the control device of the extracorporeal circulation apparatus 100. Therefore, it is clear that the program is included in the scope of the present invention. In addition, normally, the program is stored in a recording medium such as a CD-ROM, a memory card, or the like which can be read by a computer, and the program can be executed by being installed in the system. Therefore, it is clear that the recording medium is also included in the scope of the present invention.

The detailed description above describes a circulation apparatus and method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A circulation apparatus which causes blood of a patient to circulate outside a human body by using a circulation circuit, the apparatus comprising:
   a detector for detecting a status value related to blood while being provided on a flow path through which blood flows in the circulation circuit; and
   a processor configured to:
   determine whether or not a stable state in which the status value exhibits transition within a range set in advance is achieved after the circulation circuit starts blood circulation;
   set two threshold values which respectively regulate an upper end and a lower end of a permissible state range based on the status value in the stable state when it is determined that the stable state is achieved;
   monitor whether or not the status value is within the permissible state range which is regulated by the two threshold values, after the stable state is achieved;
   issue an alarm when deviation of the status value from the permissible state range is detected;
   determine, after it is determined that the stable state is achieved, whether or not an acquired differential value of the status value with respect to a time axis, for a predetermined number of consecutive acquired differential values, is above a threshold value range set in advance;
   issue the alarm when it is determined that the acquired differential value of the status value with respect to the time axis, for the predetermined number of consecutive acquired differential values, is above the threshold value range set in advance;

determine, after it is determined that the stable state is achieved, whether or not the acquired differential value of the status value with respect to the time axis, for the predetermined number of consecutive acquired differential values, is below the threshold value range set in advance; and issue the alarm when it is determined that the acquired differential value of the status value with respect to the time axis, for the predetermined number of consecutive acquired differential values, is below the threshold value range set in advance.

2. The circulation apparatus according to claim 1, wherein the processor is further configured to detect volume of blood flowing inside the circulation circuit per unit time.

3. The circulation apparatus according to claim 1, wherein the processor is further configured to detect pressure related to blood flowing inside the circulation circuit.

4. The circulation apparatus according to claim 1, wherein the processor is further configured to detect a temperature of blood flowing inside the circulation circuit.

5. The circulation apparatus according to claim 1, wherein the processor is further configured to detect volume of blood flowing inside the circulation circuit per unit time, or pressure related to blood flowing inside the circulation circuit, or a temperature of blood flowing inside the circulation circuit.

6. A method of controlling a circulation apparatus which causes blood of a patient to circulate outside a human body using a circulation circuit, the method comprising:

a detecting step of detecting a status value related to blood while being performed on a flow path through which blood flows in the circulation circuit;

a determining step of determining whether or not a stable state in which the status value exhibits transition within a range set in advance is achieved after the circulation circuit starts blood circulation;

a setting step of setting two threshold values which respectively regulate an upper end and a lower end of a permissible state range based on the status value in the stable state when it is determined that the stable state is achieved through the determining step;

a monitoring step of monitoring whether or not the status value is within the permissible state range which is regulated by the two threshold values, after the stable state is achieved; and a warning step of issuing an alarm when it is detected that the status value deviates from the permissible state range through the monitoring step;

a second monitoring step of determining, after it is determined that the stable state is achieved, whether or not an acquired differential value of the status value with respect to a time axis, for a predetermined number of consecutive acquired differential values, is above a threshold value range set in advance;

a second warning step of issuing the alarm when it is determined that the acquired differential value of the status value with respect to the time axis, for the predetermined number of consecutive acquired differential values, is above the threshold value range set in advance;

a third monitoring step of determining, after it is determined that the stable state is achieved, whether or not the acquired differential value of the status value with respect to the time axis, for the predetermined number of consecutive acquired differential values, is below the threshold value range set in advance; and a third warning step of issuing the alarm when it is determined that the acquired differential value of the status value with respect to the time axis, for the predetermined number of consecutive acquired differential values, is below the threshold value range set in advance.

7. The method according to claim 6, wherein the detecting step detects volume of blood flowing inside the circulation circuit per unit time.

8. The method according to claim 6, wherein the detecting step detects pressure related to blood flowing inside the circulation circuit.

9. The method according to claim 6, wherein the detecting step detects a temperature of blood flowing inside the circulation circuit.

10. The method according to claim 6, wherein the detecting step detects volume of blood flowing inside the circulation circuit per unit time, or pressure related to blood flowing inside the circulation circuit, or a temperature of blood flowing inside the circulation circuit.

11. A non-transitory, tangible computer readable recording medium storing a program which, when executed by a computer, causes the computer to control a circulation apparatus which causes blood of a patient to circulate outside a human body using a circulation circuit by performing the following steps:

a detecting step of detecting a status value related to blood while being performed on a flow path through which blood flows in the circulation circuit;

a determining step of determining whether or not a stable state in which the status value exhibits transition within a range set in advance is achieved after the circulation circuit starts blood circulation;

a setting step of setting two threshold values which respectively regulate an upper end and a lower end of a permissible state range based on the status value in the stable state when it is determined that the stable state is achieved through the determining step;

a monitoring step of monitoring whether or not the status value is within the permissible state range which is regulated by the two threshold values, after the stable state is achieved; and a warning step of issuing an alarm when it is detected that the status value deviates from the permissible state range through the monitoring step;

a second monitoring step of determining, after it is determined that the stable state is achieved, whether or not an acquired differential value of the status value with respect to a time axis, for a predetermined number of consecutive acquired differential values, is above a threshold value range set in advance;

a second warning step of issuing the alarm when it is determined that the acquired differential value of the status value with respect to the time axis, for the predetermined number of consecutive acquired differential values, is above the threshold value range set in advance;

a third monitoring step of determining, after it is determined that the stable state is achieved, whether or not the acquired differential value of the status value with respect to the time axis, for the predetermined number of consecutive acquired differential values, is below the threshold value range set in advance; and a third warning step of issuing the alarm when it is determined that the acquired differential value of the status value with respect to the time axis, for the predetermined number of consecutive acquired differential values, is below the threshold value range set in advance.

12. The non-transitory, tangible computer readable recording medium according to claim 11, wherein the detecting step detects volume of blood flowing inside the circulation circuit per unit time.

13. The non-transitory, tangible computer readable recording medium according to claim 11, wherein the detecting step detects pressure related to blood flowing inside the circulation circuit.

14. The non-transitory, tangible computer readable recording medium according to claim 11, wherein the detecting step detects a temperature of blood flowing inside the circulation circuit.

15. The non-transitory, tangible computer readable recording medium according to claim 11, wherein the detecting step detects volume of blood flowing inside the circulation circuit per unit time, or pressure related to blood flowing inside the circulation circuit, or a temperature of blood flowing inside the circulation circuit.

* * * * *